United States Patent [19]

Chin

[11] Patent Number: 4,721,507

[45] Date of Patent: Jan. 26, 1988

[54] SHEAR FORCE GAUGE AND METHOD AND APPARATUS FOR LIMITING EMBOLECTOMY SHEAR FORCE

[75] Inventor: Albert K. Chin, Palo Alto, Calif.

[73] Assignee: Thomas J. Fogarty, Palo Alto, Calif.

[21] Appl. No.: 872,048

[22] Filed: Jun. 5, 1986

[51] Int. Cl.⁴ .............................................. A61M 25/00
[52] U.S. Cl. ............................... 604/100; 128/774; 128/344; 73/862.39
[58] Field of Search ............... 128/774, 1 R, 344; 73/862.39, 862.62; 267/69, 73, 74; 604/96, 97, 100

[56] References Cited

U.S. PATENT DOCUMENTS

| | | | |
|---|---|---|---|
| 326,067 | 9/1885 | Sturtevant | 73/862.39 |
| 554,969 | 2/1896 | Austin | 267/74 |
| 1,012,994 | 12/1911 | Dixon et al. | 267/73 |
| 1,330,705 | 2/1920 | Herrick | 73/862.42 |
| 3,016,741 | 1/1962 | Kulp | 73/862.42 |
| 3,211,150 | 10/1965 | Foderick | 604/97 |
| 3,435,826 | 4/1969 | Fogarty | 128/344 |
| 3,543,759 | 12/1970 | McWhorter | 604/100 |
| 3,978,863 | 9/1976 | Fettel et al. | 128/348.1 |
| 4,089,337 | 5/1978 | Kronner | 604/96 |
| 4,133,303 | 1/1979 | Patel | 604/280 |

FOREIGN PATENT DOCUMENTS 0190092 6/1957 Fed. Rep. of Germany ... 73/862.39

*Primary Examiner*—Stephen C. Pellegrino
*Assistant Examiner*—Ralph Lewis
*Attorney, Agent, or Firm*—Limbach, Limbach & Sutton

[57] ABSTRACT

A shear force gauge for applying tension to an elongate wire or a catheter element and continuously sensing the amount of such tension. The gauge comprises a clamp adapted to frictionally engage the elongate element and a spring gauge secured to the clamp to apply tension thereto. In the preferred embodiment, the clamp is adjustable to permit the elongate element to slip relative thereto upon reaching a predetermined tension limit.

6 Claims, 3 Drawing Figures

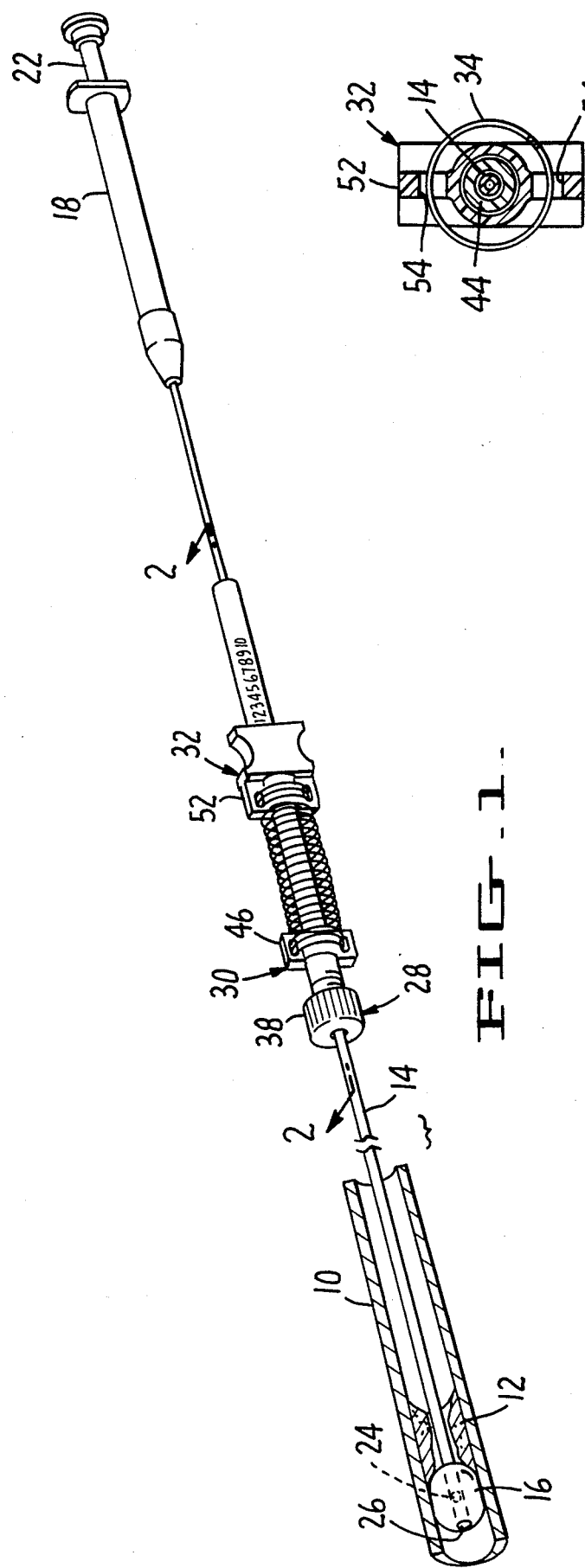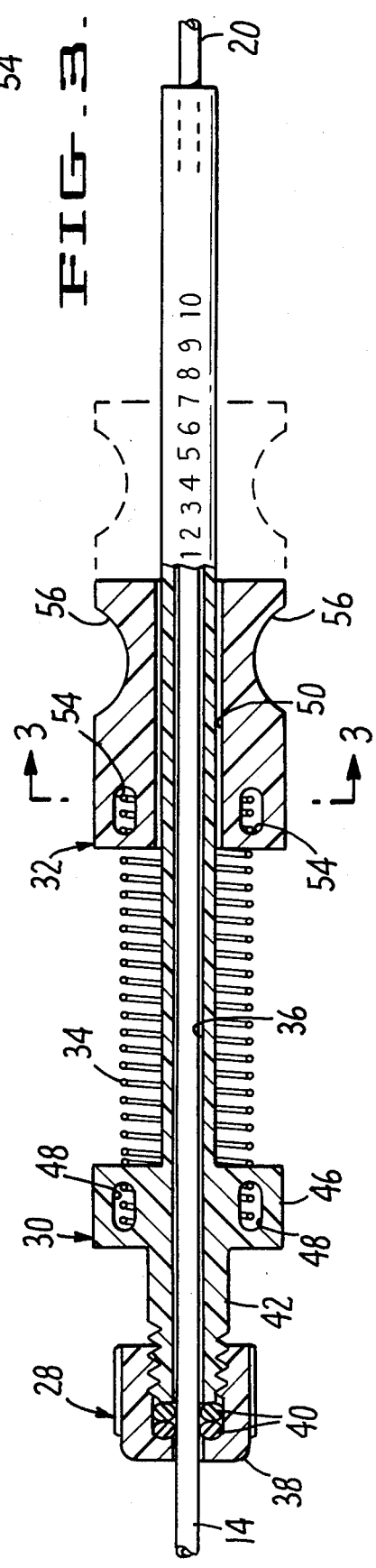

SHEAR FORCE GAUGE AND METHOD AND APPARATUS FOR LIMITING EMBOLECTOMY SHEAR FORCE

BACKGROUND OF THE INVENTION

The present invention relates to a shear force gauge for use with elongate catheter and wire elements to monitor the amount of tension applied thereto and, in the preferred embodiment, limit that tension. It is particularly concerned with such a gauge which may be used in an improved embolectomy apparatus and method to limit the amount of shear force exerted on the wall of an artery during the embolectomy process.

The prior art teaches controlling the inflation of expansible tip balloon catheters (see, for example, Foderick U.S. Pat. No. 3,211,150). It is also known to use balloon catheters for embolectomy purposes. See Fogarty U.S. Pat. No. 3,435,826 and Fettel Pat. No. 3,978,863. The latter patent is particularly interesting in that it discloses an apparatus and method for monitoring and controlling the inflation of an embolectomy balloon. External indicators to show the inflation of an internal balloon in a urinary catheter are also known (see, for example, McWhorter U.S. Pat. No. 3,543,759).

While the above prior art teaches embolectomy catheters and methods and apparatuses for controlling the inflation of a catheter balloon, it does not teach the concept of measuring the tension of the catheter on an embolectomy balloon to monitor and limit the shear force applied to an artery during embolectomy catheter use.

SUMMARY OF THE INVENTION

In its broadest aspects, the apparatus of the invention is concerned with a shear force gauge for applying controlled tension to an elongate wire or catheter element. The gauge comprises a first means to grip the element, a second means secured to the first means to apply tension to an elongate element gripped by the first means, and a third means operatively associated with the second means to sense the force applied to the first means through the second means. The third means may comprise a tension gauge and/or a friction clamp. The clamp in the preferred embodiment is adjustable and adaptable to limit the tension force which may be applied to the elongate element.

It is a principal object of the invention to provide a shear force gauge which may be used with an embolectomy catheter to limit the shear force exerted on an artery during an embolectomy process.

Another object of the invention is to provide such a gauge which may be used to continuously monitor the tension applied to an embolectomy catheter and limit the amount of such tension.

Still another object is to provide such a gauge which is of simple construction and may be readily applied to existing embolectomy catheters without modification of the catheter.

Yet another object of the invention is to provide such a gauge which may be adjusted to limit the amount of tension applied therethrough.

Another object of the invention is to provide an embolectomy apparatus and method wherein shear force exerted on an artery during embolectomy may be monitored and limited.

The foregoing and other objects will become more apparent when viewed in light of the accompanying drawings and following detailed description.

BRIEF DESCRIPTION OF THE DRAWINGS

FIG. 1 is a perspective view of an embolectomy catheter embodying the shear force gauge of the present invention, with the catheter shown in the process of removing an embolus from an artery;

FIG. 2 is a cross-sectional view of the shear force gauge, taken on the plane designated by line 2—2 of FIG. 1; and FIG. 3 is a cross-sectional view taken on the plane designated by line 3—3 of FIG. 2.

DESCRIPTION OF THE PREFERRED EMBODIMENT

Referring now to FIG. 1, an artery 10 having an embolus 12 therein is shown in the process of being treated by an embolectomy catheter embodying the method and apparatus of the present invention. The catheter is designated by the numeral 14 and has an inflatable balloon 16 secured thereto proximate its distal end and an inflation syringe 18 secured thereto at its proximal end. The catheter 14, balloon 16 and syringe 18 are of conventional construction, such as may be seen in prior Fogarty U.S. Pat. No. 3,435,826. A lumen 20 extends through the full length of the catheter. The balloon 16 and syringe 18 are both in fluid communication with the lumen whereby the plunger 22 of the syringe may be compressed to apply fluid pressure to the interior of the balloon for balloon inflation. A small port 24 provides for communication between the interior of the balloon and the through lumen. The distal end, designated 26, of the catheter is sealed so as to prevent the escape of fluid from the through lumen.

The principal elements of the shear force gauge comprise a first or clamp element 28 adapted to grip the catheter, a second or intermediate element 30 threadably secured to the clamp element to apply force thereto and tension the catheter; and a third or tension applying and sensing element 32 secured to the element 30 by a coil spring 34. As can be seen from FIG. 2, the element 30 is of an elongate tubular configuration with a bore 36 formed longitudinally therethrough. The catheter 14 extends through this bore.

The element 28 takes the form of a compression nut 38 having a pair of O-rings 40 received therein in concentric relation to the catheter 14. The amount of tension which may be applied to the catheter 14 through the clamp element 28 may be adjusted by select adjustment of the amount of compression applied to the O-rings by the nut 38. Such adjustment provides for slippage of the catheter relative to the O-rings when the tension exceeds a predetermined adjusted limit.

The intermediate element 30 comprises a forward end 42 on which the screw threads received within the compression nut are formed, and an elongate tubular rearward end 44. The latter end is formed within numerical indicia along the length thereof which, in cooperation with the element 32, serve as means to measure the tension applied to the catheter 14 through the gauge. An enlarged boss 46 is formed on the element 30 intermediate the ends 42 and 44 and is formed with openings 48 for receipt of the coils of the spring 34. Through the latter boss and openings, the spring is secured in tension-imparting relationship to the element 30.

The element 32 is slidably received on the rearward end 44 of the element 30. A passage 50 extending through the element 32 accommodates such slidable receipt. The forward end of the element 32 is formed with an enlarged boss 52 formed with openings 54 therethrough for receipt of the coils of the spring 34. Through the latter openings, the spring is secured in tension-imparting relationship to the element 32 and tension applied to the element 32 is transmitted to the element 30 through the spring. Finger grooves 56 formed in the outer surface of the element 32 facilitate the manual application of tension to the element.

In use, the tension gauge is applied to the embolectomy catheter by sliding the gauge over and into concentric relationship with the catheter while the balloon 16 is in a deflated condition. This results in the catheter and gauge being assembled into the condition shown in FIG. 1. Then the gauge is slid to the desired position along the length of the catheter and the compression nut 38 is adjusted to secure the clamp element 28 to the catheter with the desired degree of gripping force. This force may be measured by pulling on the element 32 while holding the distal end of the catheter secure. Such measurement will be indicated by the position of the element 32 relative to the numerical indicia on the rearward end 44 of the element 30.

With the gauge and catheter so assembled, the embolectomy process is carried out by directing the catheter through the artery to be treated and past the embolus therein, with the balloon 16 in a deflated condition. Once the catheter and balloon are so positioned, as seen in FIG. 1, the balloon is inflated by compressing the plunger 22. Then the catheter is withdrawn from the artery by pulling on the catheter through the finger grooves in the element 32. Such pulling functions to apply tension to the catheter 14 through the spring 34 and the clamp element 28. That tension may be continuously sensed and monitored by observing the position of the element 32 relative to the numerical indicia on the rearward end 44 of the element 30. As the shear force thus measured starts to approach the maximum desired level, the speed of withdrawal of the catheter may be altered to decrease the shear force exerted on the artery. If this is not sufficient, partial deflation of the balloon may be effected. In the event the shear force somehow exceeds the predetermined maximum degree permitted by the clamp element 28, the clamp element will permit the catheter to slide relative thereto.

CONCLUSION

From the foregoing detailed description, it is believed apparent that the present invention enables the attainment of the objects initially set forth herein. In particular, the invention provides means for limiting the shear force exerted on a vessel wall by an embolectomy catheter. Thus, damage of the arterial endothelium and the possible formation of intimal flaps is avoided.

While a preferred embodiment of the invention in an embolectomy catheter has been shown, it is to be understood that the invention is not intended to be limited to this embodiment. For example, the gauge may also find use in applying tension to elongate elements other than catheters, such as the wires used to support calibrating catheters and other instruments. It is also anticipated that the shear force gauge may be used with other balloon catheters (for example, in the biliary system, to probe the bile ducts). Immediate shear force measurements will decrease the incidence of injury and complications associated with the use of such balloon catheters.

I claim:

1. An improved embolectomy apparatus comprising: an elongate catheter having a through lumen; a balloon secured to the catheter proximate one end thereof in sealed fluid communication with the lumen; a syringe secured to the catheter proximate the other end thereof in sealed fluid communication with the lumen; first means slidably carried by the catheter to selectively grip the catheter through frictional engagement therewith, said apparatus including means to adjust the degree of frictional engagement between the first means and the catheter to permit the first means to slip relative to the catheter to limit the tension applied to the catheter; second means secured to the first means to apply force thereto and tension to a catheter gripped thereby; and third means operatively associated with the second means to sense the force applied to the first means through the second means.

2. An improved embolectomy apparatus according to claim 1 wherein: the first means comprises a tube through which the catheter is extended; the second means is slidably received on said tube and secured to the first means through a deflectable spring; and the third means comprises a gauge to measure movement of the second means relative to the first means.

3. An improved embolectomy apparatus according to claim 2 wherein the gauge comprises indicia marked along the length of the tube and a follower on the second means alignable with said indicia.

4. An improved embolectomy apparatus according to claim 1 wherein the first means comprises an annular clamp through which the catheter extends and means to selectively compress the clamp into engagement with the catheter with varying degrees of force.

5. An improved embolectomy method comprising: providing an elongate catheter having a through lumen and a balloon proximate the distal end thereof in sealed fluid communication with the lumen; directing said catheter through a body passage and past an embolus in the passage; inflating the balloon by applying fluid pressure thereto through the catheter lumen; withdrawing the catheter from the body passage by gripping the catheter and applying tension thereto; continuously monitoring the tension applied to the catheter during such withdrawal; and controlling the withdrawal force applied to the catheter to maintain the tension applied to the catheter within a predetermined limit.

6. An improved embolectomy method according to claim 5 wherein the catheter is gripped through a frictional connection which maintains the withdrawal force applied to the catheter beneath a predetermined level.

* * * * *